United States Patent
Le et al.

(10) Patent No.: US 10,350,113 B2
(45) Date of Patent: Jul. 16, 2019

(54) HEADSET

(71) Applicant: Tactical Command Industries, Inc., Brentwood, CA (US)

(72) Inventors: David Trinh Le, Irvine, CA (US); John Brad Medine, Chino, CA (US); Todd Roger Mussell, Rancho Cucamonga, CA (US)

(73) Assignee: Safariland, LLC, Jacksonville, FL (US)

( * ) Notice: Subject to any disclaimer, the term of this patent is extended or adjusted under 35 U.S.C. 154(b) by 474 days.

(21) Appl. No.: 15/163,936

(22) Filed: May 25, 2016

(65) Prior Publication Data

US 2017/0340046 A1    Nov. 30, 2017

(51) Int. Cl.
| | | |
|---|---|---|
| H04R 1/10 | (2006.01) | |
| A61F 11/06 | (2006.01) | |
| A42B 3/16 | (2006.01) | |

(52) U.S. Cl.
CPC .............. *A61F 11/06* (2013.01); *A42B 3/16* (2013.01); *H04R 1/105* (2013.01); *H04R 1/1066* (2013.01); *H04R 2201/023* (2013.01)

(58) Field of Classification Search
CPC .. H04R 1/1008; H04R 1/1066; H04R 5/0335; H04R 2201/023; H04R 2201/105; A42B 3/16; A42B 3/30; A61F 11/06; A61F 11/14

USPC ....... 381/301, 309, 370, 371, 374, 376, 379; 2/209, 422, 423, 906
See application file for complete search history.

(56) References Cited

U.S. PATENT DOCUMENTS

| | | | | |
|---|---|---|---|---|
| 3,430,261 | A | * | 3/1969 | Benner ................. A42B 3/166 2/209 |
| 5,541,816 | A | | 7/1996 | Miserendino |
| 6,965,681 | B2 | | 11/2005 | Almqvist |
| 7,317,809 | B2 | | 1/2008 | Almqvist |
| 8,166,575 | B2 | * | 5/2012 | Haselmayer ........... A42B 3/166 2/10 |
| 2008/0075314 | A1 | | 3/2008 | Chang |
| 2011/0314594 | A1 | | 12/2011 | Rogers et al. |

FOREIGN PATENT DOCUMENTS

KR    10-1289968 B1    7/2013

OTHER PUBLICATIONS

PCT Application No. PCT/IB17/000654, International Search Report and Written Opinion dated Nov. 27, 2017.

* cited by examiner

*Primary Examiner* — Huyen D Le
(74) *Attorney, Agent, or Firm* — Kane Kessler, P.C.; Paul E. Szabo (57) ABSTRACT

A headset includes two earcups that overlie and seal around the wearer's ears. The headset includes a system for suspension of the earcups on a helmet, as well as a speaker enclosure that provides increased structural strength without taking up additional space on the board.

7 Claims, 10 Drawing Sheets

HEADSET

BACKGROUND OF THE INVENTION

This application relates to a headset that includes two earcups designed to overlie and seal around the wearers ears. This type of headset is often worn by a soldier or a fire fighter or a law enforcement officer, to enable communication with colleagues. This type of headset is sometimes worn with a protective helmet, and so must be designed to accommodate such usage.

The headset of the present invention includes several inventive features. These include a system for suspension of the earcups on a helmet and a speaker enclosure, for mounting on a PC board that provides increased structural strength without taking up additional space on the board.

DETAILED DESCRIPTION

Figure 1:
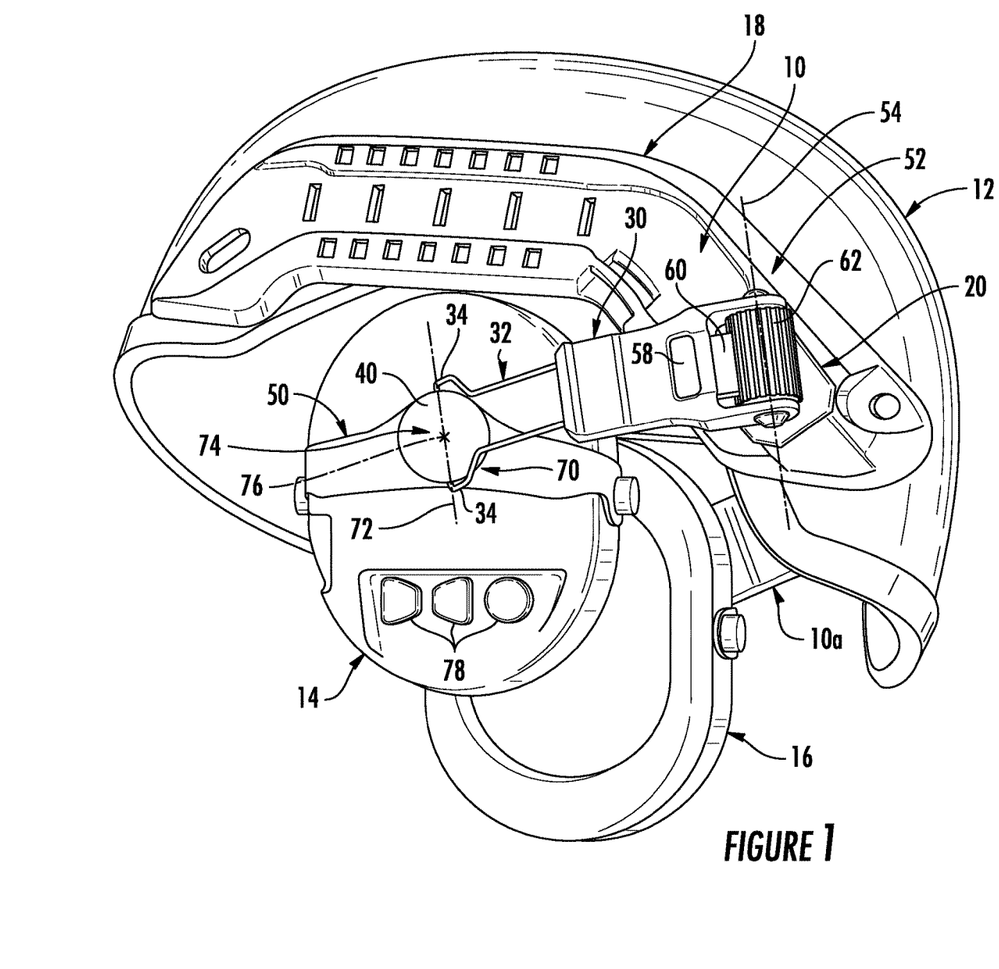
FIG. 1 is a pictorial illustration of a headset that is a first embodiment of the invention, including a left earcup shown mounted on a left side of a helmet and a right earcup mounted on a right side of the helmet.

FIG. 1 illustrates an earcup suspension assembly 10 ("assembly") that is a first embodiment of the invention. The assembly 10 is shown supported on a helmet 12. The helmet 12 could be of any configuration, and could be any head covering device. The particular helmet 12 that is illustrated does not have ear covering portions, thus allowing the assembly 10 to support an earcup on an ear at a location outside of the enclosure of the helmet. The drawings show the helmet 12 as viewed from the left side; the right side is a mirror image, typically. Two earcup suspension assemblies 10 are commonly used with one helmet 12. Thus, the drawings focus on a left side earcup suspension assembly 10 that supports a left earcup 14; a right side earcup suspension assembly 10a is a mirror image and is shown only partially in FIG. 1, supporting a right earcup 16.

The helmet 12 is shown as supporting a left side rail 18. The particular rail 18 that is illustrated is a standard ARC rail, but the invention is usable with other types of rails. Alternatively, an earcup suspension assembly 10 of the present invention can be supported on a different intermediate member or directly on a helmet 12. Thus, the term "rail" as used herein is intended to refer usually to that structure to which the earcup suspension assembly 10 is connected. The term "rail connector" can mean the portion of the assembly 10 that is fixedly supported on the helmet 12, either directly or through an intermediate piece such as a rail 18.

The assembly 10 includes a rail connector 20 that is configured for fixedly engaging the rail 20, to support the assembly on the rail. The assembly also includes a main arm 30 that extends from the rail connector 20. The main arm 30 includes a wireform element 32 that is slidable in and out to adjust the length of the main arm. The outer end 32 of the wireform element 32 is configured as two pins 34 that extend laterally toward each other into a disc 40 that forms part of the assembly 10. The disc 40 pivotally supports a bracket 50 that is secured to the earcup 16 itself. As a result, the earcup 16 is supported on the main arm 30.

The main arm 30 is supported on the rail connector 20 by two joints for movement in two different degrees of freedom. A first joint 52 (FIG. 1) between the main arm 30 and the rail connector 20 allows for a flipping motion, of the main arm relative to rail connector, about an axis 54. The first joint 52 comprises structure on the main arm 30 that engages structure on the rail connector 20. Thus, the main arm 30 can be flipped in and out relative to the rail 18 and the 12 helmet, about the axis 54; the drawings show several such positions.

The assembly 10 includes a spring (not shown) that biases the main arm 30 about the first axis 54, in a direction toward the ear, thus to keep earcup pressure on the user's head as needed. A release switch 58 on the main arm 30 controls the movement of the first joint 52. One or more ribs 60 on the main arm 30 are engageable in grooves 62 on the rail connector 20, to control the flipping motion and to set certain positions. This detent structure both limits the range of motion and avoids undesirable spinning of the earcup 14.

Figure 3A:
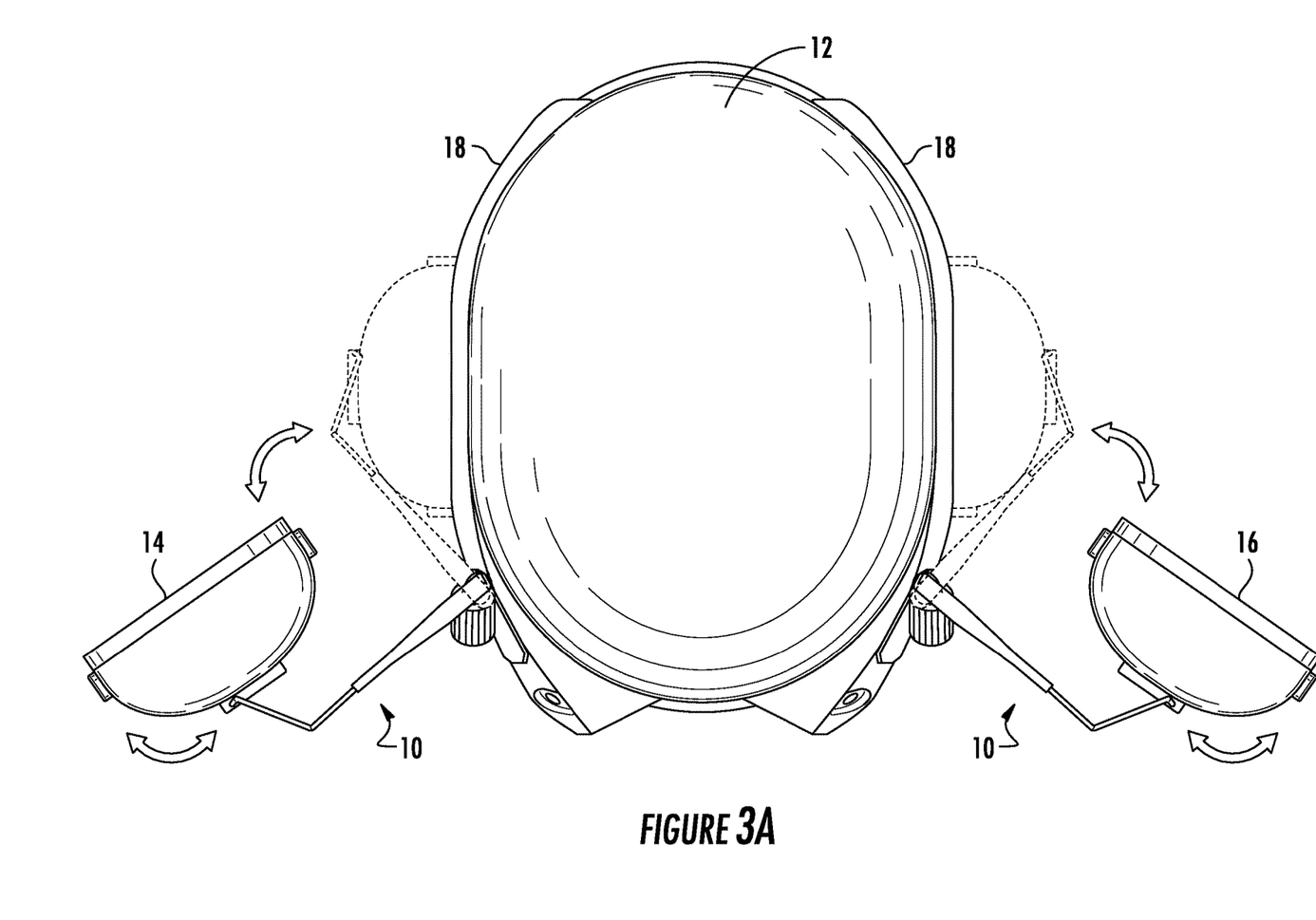
FIG. 3A is a top plan view of the helmet and the left and right earcups, showing the left and right earcups in a fourth position relative to the helmet.
Figure 3B:
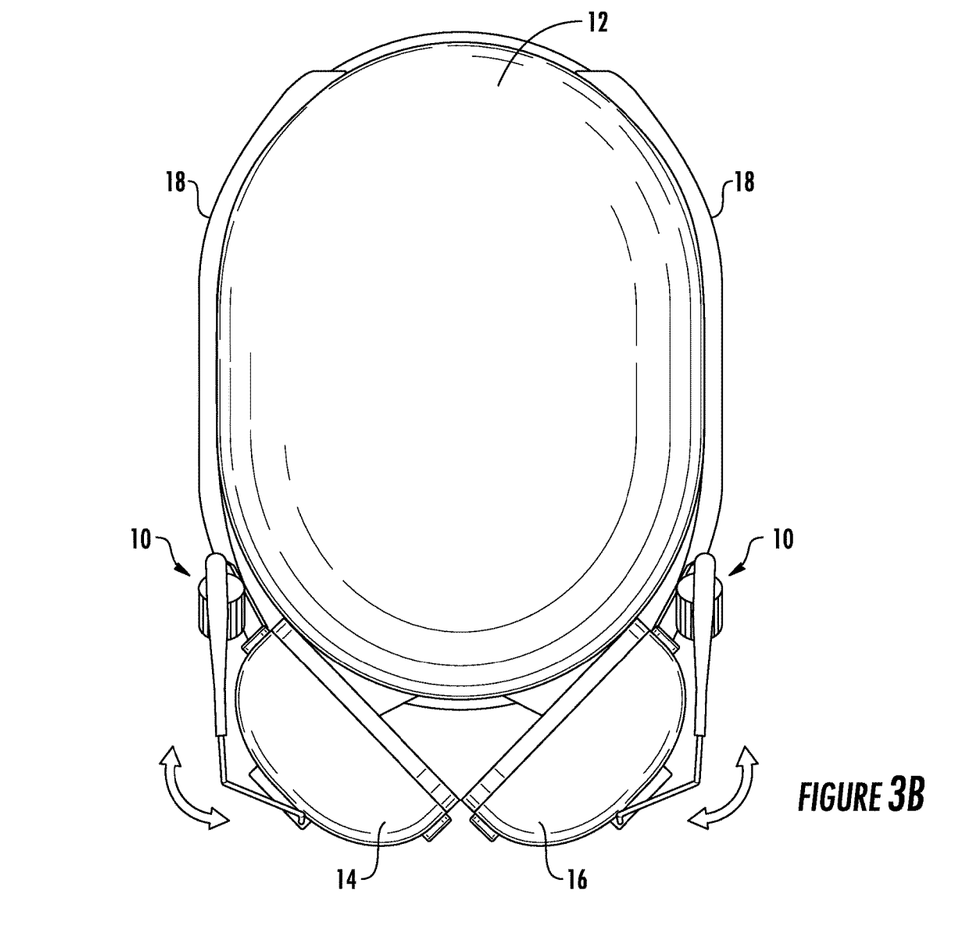
FIG. 3B is a top plan view similar to FIG. 3B, showing the left and right earcups in a fifth position relative to the helmet.

For example, FIG. 1 illustrates a position in which the earcup 14 is against the ear, and FIG. 3A illustrates a position in which the earcup is flipped back up out of the way.

Figure 2A:
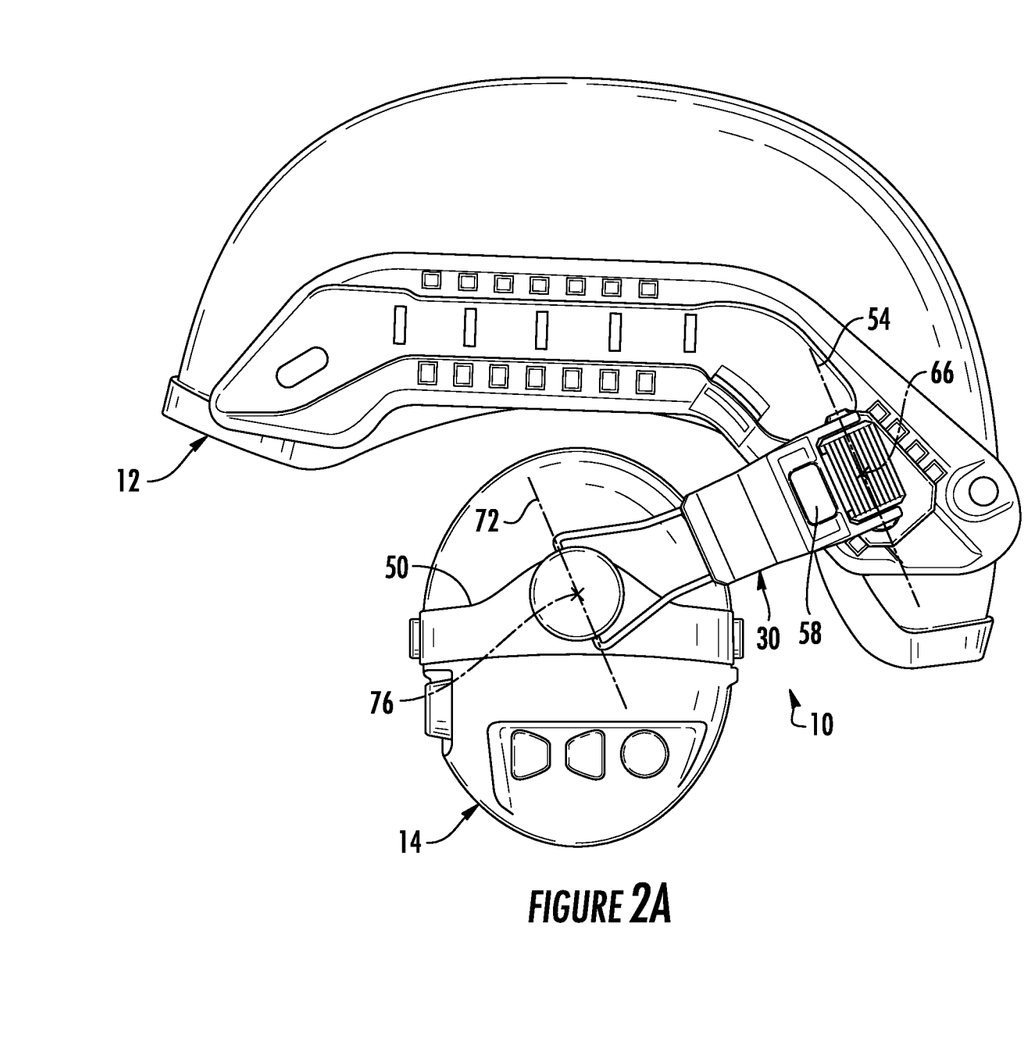
FIG. 2A is a left side elevational view of the helmet and left earcup of FIG. 1, showing the left earcup in a first position relative to the helmet.
Figure 2B:
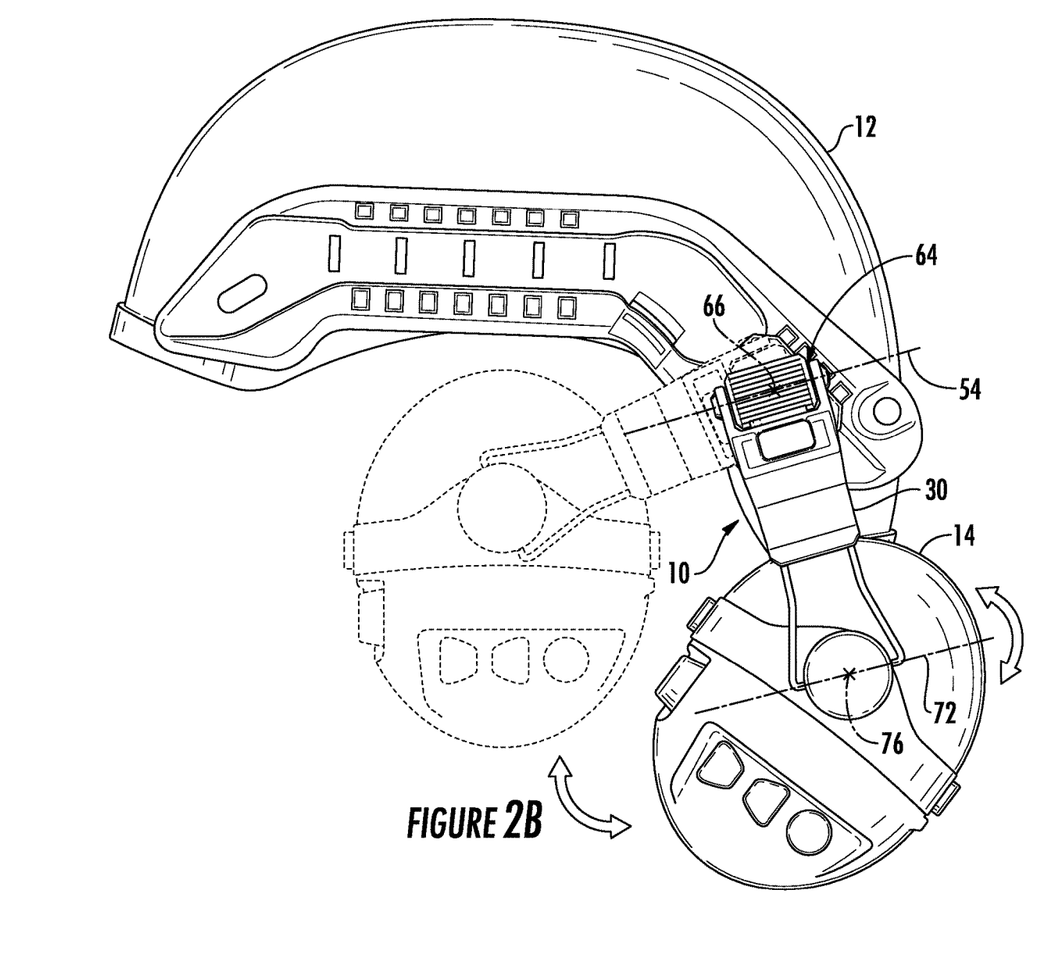
FIG. 2B is a view similar to FIG. 2A, showing the left earcup in a second position relative to the helmet.
Figure 2C:
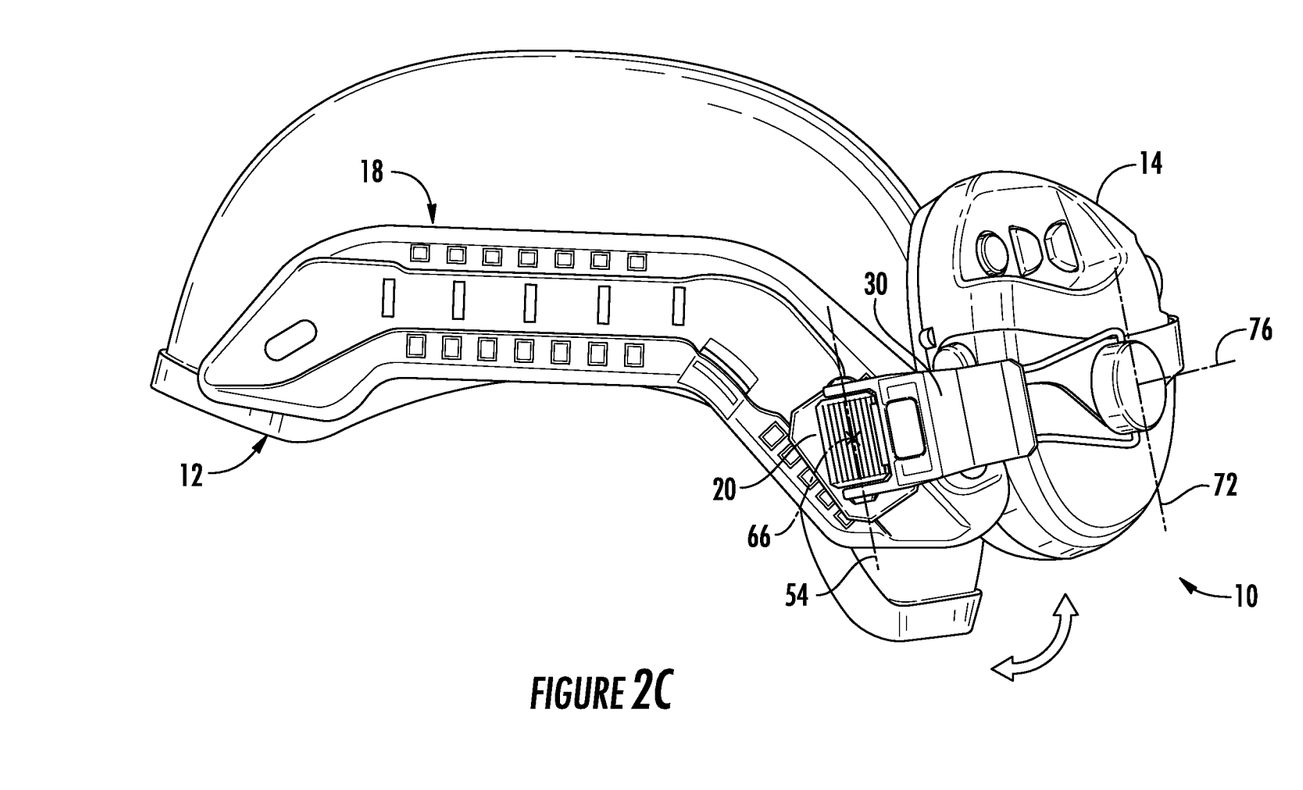
FIG. 2C is a view similar to FIG. 2A, showing the left earcup in a third position relative to the helmet.

A second joint 64 in the assembly allows for pivotal (swinging) movement of the main arm 30 relative to the rail connector 20 and thus relative to the rail 18 and the helmet 12). The second joint 64 is located between the main arm 30 and the rail connector 20. The second joint 84 comprises structure on the main arm 30 that engages structure on the rail connector 20 that define a pivot axis 86. The pivot axis 66 extends generally normal into the plane of the rail connector 20. The main arm 30 is thus pivotable about the axis 66 between a plurality of different positions, for example as shown in FIGS. 2A and 2B.

A third joint 70 in the assembly 10 provides for a third degree of freedom of movement. The third joint 70 is located between the main arm 30 and the disc and comprises structure on the main arm 30 engaging structure on the disc. Specifically, the two pins 34 of the wire form element 32 of the main arm are received in opposite sides of the disc 40 to provide for pivoting motion about an axis 72 that extends between the two pins. The third joint 70 thus supports the disc 40, as well as the earcup bracket 50 and the earcup 14 itself, for pivotal (flipping) movement relative to the main arm 30 about this axis 72.

A fourth joint 74 in the assembly 10 provides for a fourth degree of freedom of movement. The fourth joint 74 is located between the disc 40 and the bracket 50 and comprises structure on the disc engaging structure on the bracket. The bracket 50 is movable on the disc 40 in a pivoting motion about an axis 76 that extends normal to the plane of the disc and thus into the earcup 14. The fourth joint 74 thus supports the earcup bracket 50 and the earcup 14 itself for pivotal movement relative to the main arm 30 about this fourth axis 76.

As a result of the various joints and degrees of motion, the earcups 14 are movable relative to the helmet 12 in a variety of ways and to a variety of different positions, as shown in the drawings. The earcups 14 can be held snugly on the ears to maintain a tight seal against the user's head and thus provide good audio communication, even when the helmet 12 moves relative to the user's head.

The electrical connection to the earcups 14 is separate, via wires not seen, perhaps under the helmet padding inside the helmet shell. The earcups may include buttons shown schematically at 78 that control the electronics and audio.

Figure 4A:
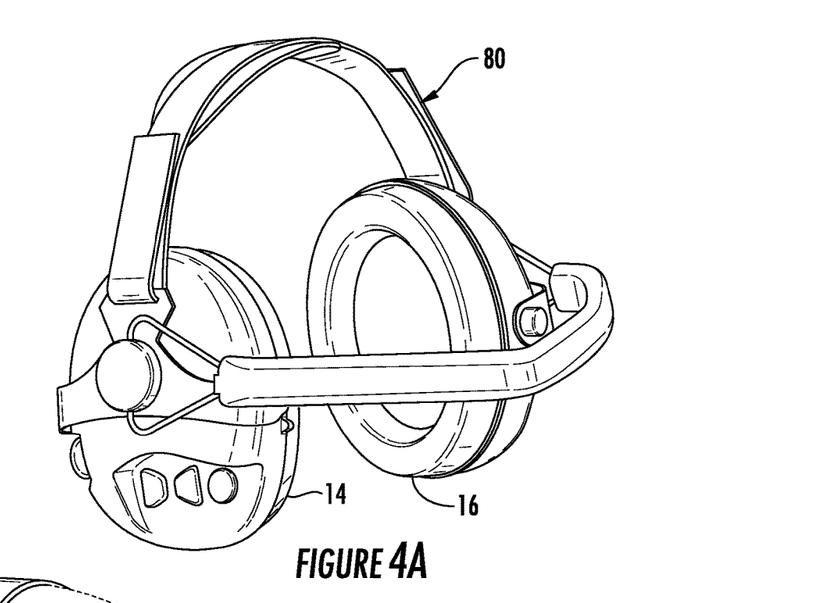
FIG. 4A is an illustration of a headset including straps holding two earcups together.
Figure 4B:
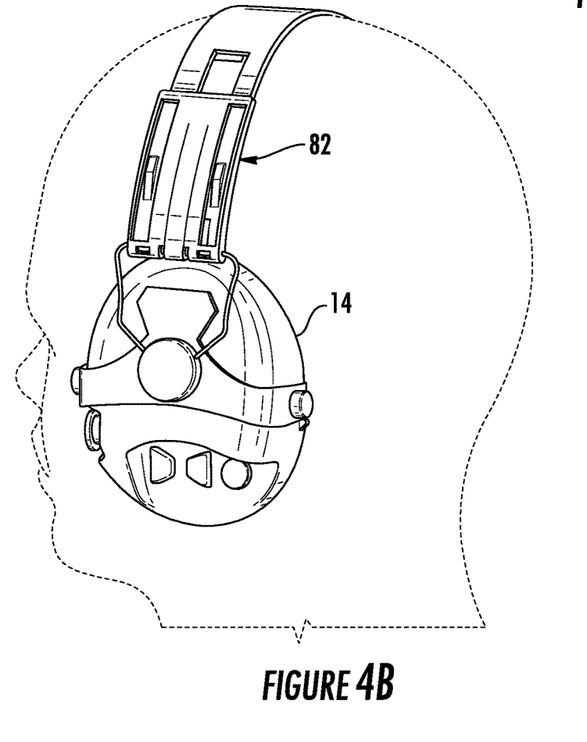
FIG. 4B is an illustration of a headset including a single band holding the two earcups together.

In alternative embodiments, earcups are suspended not on a rail of helmet. For example, FIG. 4A shows two earcups suspended via an assembly, on a webbing strap system 80. FIG. 4B shows two earcups suspended via an assembly, on a rigid but bendable plastic band 82. An earcup suspension assembly of the present invention may also be used to support earcups inside a helmet such as a firefighter's helmet that covers the ears.

In accordance with a feature of the invention, each earcup includes two speakers 90 (FIGS. 5 and 6) mounted on a printed circuit (PC) board (FIGS. 7A and 7B) that is incorporated in the earcup. The two speakers 90 are, in the illustrated embodiment, identical to each other in physical configuration and size, for economy of manufacture in other embodiments, the two speakers 90 could be different, and could nave two different electronic components. Other earcups may use only one speaker.

Each speaker 90 includes a plastic housing 92. A circular central portion 94 of the housing 92 encloses the electrical components (not shown) of the speaker. The front or top face (FIG. 5) of the central portion 94 has openings 96 for sound to be emitted. The back or bottom face (FIG. 6) of the speaker 80 has contacts 98 adapted to electrically connect the speaker with the PC board.

Figure 5:
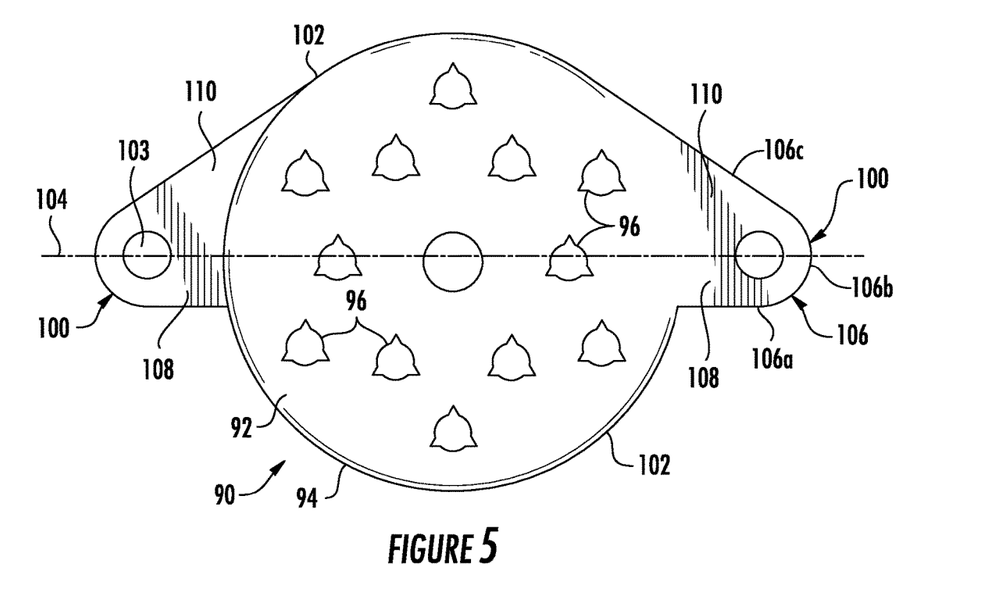
FIG. 5 is a top plan view of a speaker in accordance with the present invention and that is used in the earcup.
Figure 6:
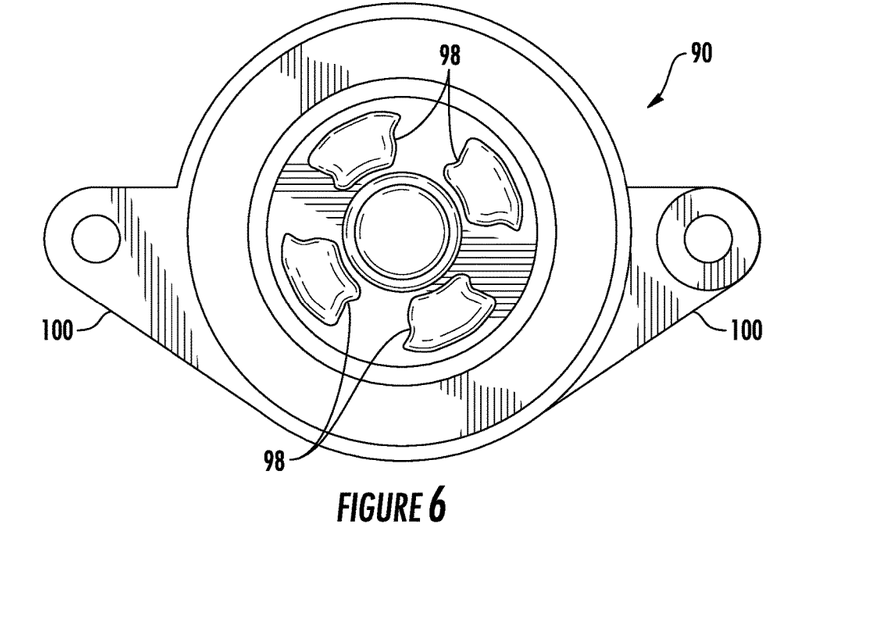
FIG. 6 is a bottom plan view of the speaker of FIG. 5.
Figure 7A:
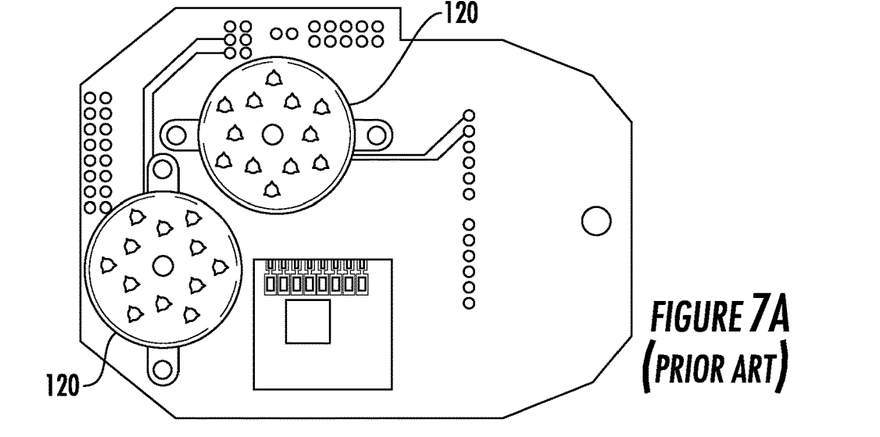
FIG. 7A is a view of a printed circuit board including a prior art speaker.

The speaker has two mounting portions 100. The mounting portions 100 are located diametrically opposite each other on the outer periphery 102 of the central portion 94. The mounting portions 100 extend or project from the circular central portion 94. The mounting portions 100 are mirror images of each other.

Each mounting portion 100 has a fastener opening 103 for receiving therethrough a fastener, typically a screw, to fasten the speaker to the PC board. The fastener openings 103 are located on a centerline 104 of the speaker 90.

Each mounting portion 100 has an outer edge surface 106 that extends from the circular outer periphery 102 of the central portion 94 as a continuation of the outer periphery of the central portion. The outer edge surface 106 includes a first segment 106a that extends from the outer periphery 102 in a direction parallel to the centerline 104 and just past the fastener opening 102. A second segment 106b of the outer edge surface 106 of the mounting portion 100 is formed as a circular arc extending from the first segment 106a and around to the opposite side of the fastener opening 103. A third segment 106c of the outer edge surface 106 of the mounting portion 100 extends in a straight line from the second segment 106b back to the central portion periphery 102. The third segment 106c lies tangent to the circular outer periphery 102 of the central portion 94.

As a result of this configuration, each mounting portion 100 of the speaker 90 effectively has two sections 108 and 110, on opposite sides of the centerline 104 of the speaker. The first section 108, which is bounded by the first edge surface segment 106a, is relatively small. The second section 110, which is bounded by the third edge surface segment 106c, is much larger in area and mass than the first section 108.

Because of the extra area and mass of the second section 110, the speaker 90 has significantly greater structural strength in its mounting portions 100, as compared to the prior art speaker 120 (FIG. 7A) which includes only two first sections. As a result of this increased mass and structural strength of the speaker mounting portions 100, there is less chance that they will crack if assembled improperly, if the mounting screw is overly tightened, for example.

Figure 7B:
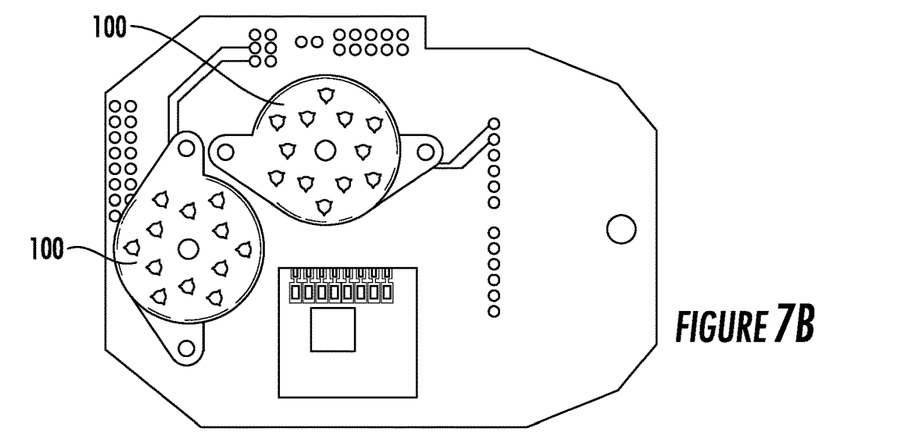
FIG. 7B is a view of the printed circuit board including two of the speakers of FIG. 5 shown mounted in a first orientation relative to each other.
Figure 7C:
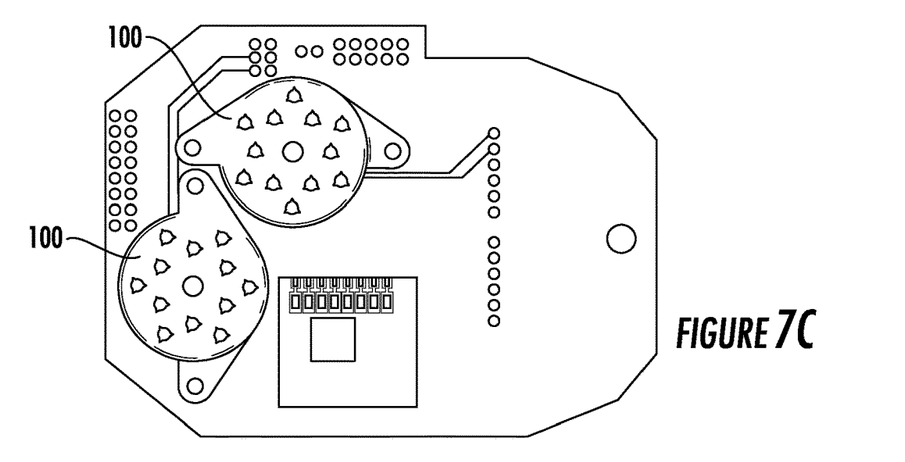
FIG. 7C is a view similar to FIG. 7B and showing two of the speakers of FIG. 5 shown mounted in a second orientation relative to each other.

This increase in strength does not affect usability in an environment that calls for two speakers 100 mounted side by side on a PC board, such as the earcup 14 of the present invention. Because the extra structure is present on only one side of the speaker centerline 104 rather than both, there are various possibilities for placing two speakers 100 of the present invention close together without interference. Two such two possibilities are shown in FIGS. 7B and 7C.

In accordance with another feature of the invention, each earcup 14 can accept either one of two different sizes (types) of commonly used batteries—in this case, AAA batteries or CR-123 (photocell) batteries. As a result, the earcup 14 is more likely to be usable with whatever batteries the user happens to have on hand. AAA batteries are about 45 mm long and about 10.5 mm in diameter. A CR-123 battery is about 34 mm long and about 17 mm in diameter. This feature of the invention is also usable with other types and sizes of batteries.

There is an openable cover 130 (FIG. 8A) on the earcup 14 that forms one end of a chamber 132 in the earcup. First electrical contacts (not shown) are on the inner surface of the cover. At the end of the chamber 132 opposite the cover 130 are a set of second electrical contacts (not shown). The first and second electrical contacts are spaced apart from each other by a distance that is substantially equal to the distance between the terminals on opposite ends of a AAA battery. The chamber 132 can accept two AAA batteries 134 side by side extending the length of the case. The first and second electrical contacts are electrically connected to the electrically powered components of the earcup 14. Thus the AAA batteries 134 can power the earcup.

Figures 8A, 8B:
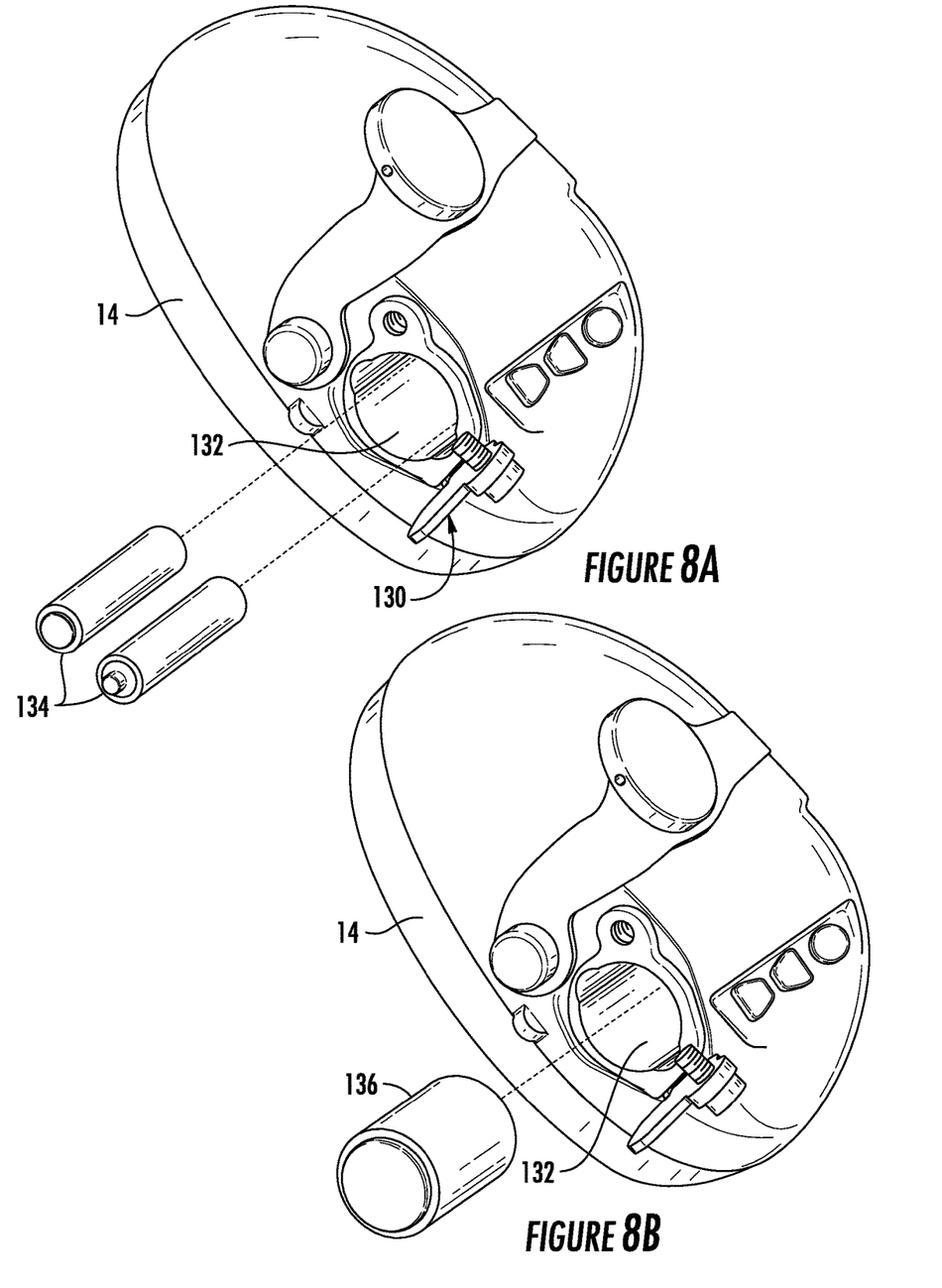
FIG. 8A is an illustration of an earcup with a battery compartment cover open and showing two AAA batteries ready for loading into the compartment.
FIG. 8B is an illustration similar to FIG. 8A and showing one CR-123 battery ready for loading into the compartment.

The compartment can alternatively accept one CR-123 (photocell) battery 136 extending in the same direction as the two AAA batteries 134 would extend. To accomplish this, another set of contacts (not shown) projects inward from the chamber end wall and from the cover 130 to accommodate the shorter battery 134. Therefore, when this single battery 136, which is wider but shorter than the AAA batteries 134, is inserted into the compartment, the single battery can power the earcup 14. Alternatively, the battery or batteries can be placed in a removable battery case that is placed in a compartment in the earcup 14.

The invention claimed is:

1. An earcup suspension assembly configured for use with a helmet, the earcup suspension assembly comprising;
   a helmet connector configured for fixed connection to the helmet thereby to support the assembly on the helmet;
   a main arm extending from the helmet connector;
   a first joint between the helmet connector and the main arm, the first joint supporting the main arm on the helmet connector for pivotal movement relative to the helmet connector about a first axis;
   an earcup bracket extending from the main arm, the earcup bracket being configured to connect with and support an earcup; and
   a second joint between the main arm and the earcup bracket, the second joint supporting the earcup bracket on the main arm for pivotal movement relative to the main arm about a second axis;
   further comprising a third joint between the main arm and the helmet connector and at the location of the first joint, enabling flipping movement of the main arm about the third joint in a direction toward and away from the ear of a wearer of the helmet.

2. An earcup suspension assembly as set forth in claim 1 comprising a biasing member acting between the main arm and the helmet connector thereby to bias the main arm about the third joint in a direction toward the ear of a wearer of the helmet.

3. An earcup suspension assembly as set forth in claim 2 further comprising a fourth joint between the main arm and the earcup bracket and at the location of the second joint, the fourth joint enabling flipping movement of the earcup bracket about the fourth joint in a direction toward and away from the ear of a wearer of the helmet.

4. An earcup suspension assembly as set forth in claim 1 wherein the helmet connector is an ARC rail.

5. An earcup suspension assembly as set forth in claim 1 wherein the third joint includes a release switch on the main arm that controls the movement of the first joint.

6. An earcup suspension assembly as set forth in claim 5 further including a detent structure to control the flipping motion of the earcup.

7. An earcup suspension assembly as set forth in claim 1 wherein the second joint comprises pins on a wireform element that is part of the main arm.

\* \* \* \* \*